United States Patent [19]
Cunningham et al.

[11] Patent Number: 6,117,134
[45] Date of Patent: Sep. 12, 2000

[54] INSTRUMENT FOR SUCTION ELECTROSURGERY

[76] Inventors: James Steven Cunningham, 910 Portland Pl., #20, Boulder, Colo. 80304; Terry Matthew Duffin, 18802 E. Chenango Pl., Aurora, Colo. 80015; Dennis John Harvilla, 804 Harrison Dr., Lafayette, Colo. 80026

[21] Appl. No.: 08/601,389

[22] Filed: Feb. 14, 1996

[51] Int. Cl.$^7$ .................................................. A61B 17/39
[52] U.S. Cl. ............................................. 606/49; 604/35
[58] Field of Search .................... 606/2, 32, 41, 606/45, 46, 49; 604/35

[56] References Cited

U.S. PATENT DOCUMENTS

| | | |
|---|---|---|
| 3,828,780 | 8/1974 | Morrison, Jr. . |
| 4,686,981 | 8/1987 | Forintos . |
| 4,899,742 | 2/1990 | Muller ..................... 606/180 |
| 5,275,612 | 1/1994 | Bales, Jr. ................. 128/751 |

*Primary Examiner*—Jennifer Bahr
*Assistant Examiner*—Rosiland Kearney

[57] ABSTRACT

An instrument for suction and electrosurgery has an elongate body molded of a polymer. A main flow passage extends through the length of the body. A hollow metal aluminum tube extends from the body and attaches to electrosurgical power and is in fluid communication with the passage. The tube extends from the body to the patient passing energy thereto. An open distal end on the body receives the tube on a shelf thereacross to engage and hold the tube. The shelf has opposed tapered camming surfaces and an edge axially spaced proximally within the opened distal end. The edge engages with a spade connector on an insulated cable coupled to the power during insertion of the tube to fold back the spade connector as the tube is received. The camming surface captures the folded spade connector against the tube inserted in a generally cylindrically surround and against the camming surface so radial forces on the inserted tube are equal in radial directions and compression between the inside of the surround and the tube. An interior portion defined by the surround and the shelf receives the tube so the main flow passage is in fluid communication with the tube for transmission of suction. The spade connector at the shelf end of the insulated cable bends to wrap around the edge of the shelf for capture within the interior portion between the camming surface and the tube.

11 Claims, 2 Drawing Sheets

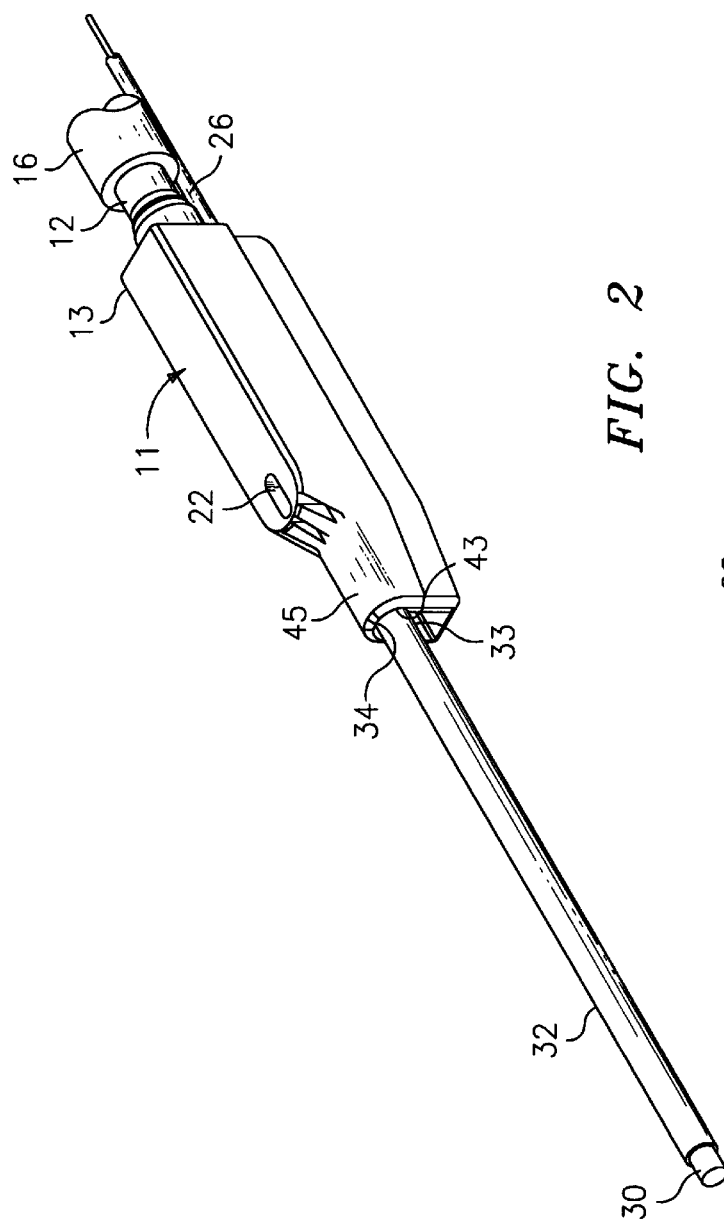
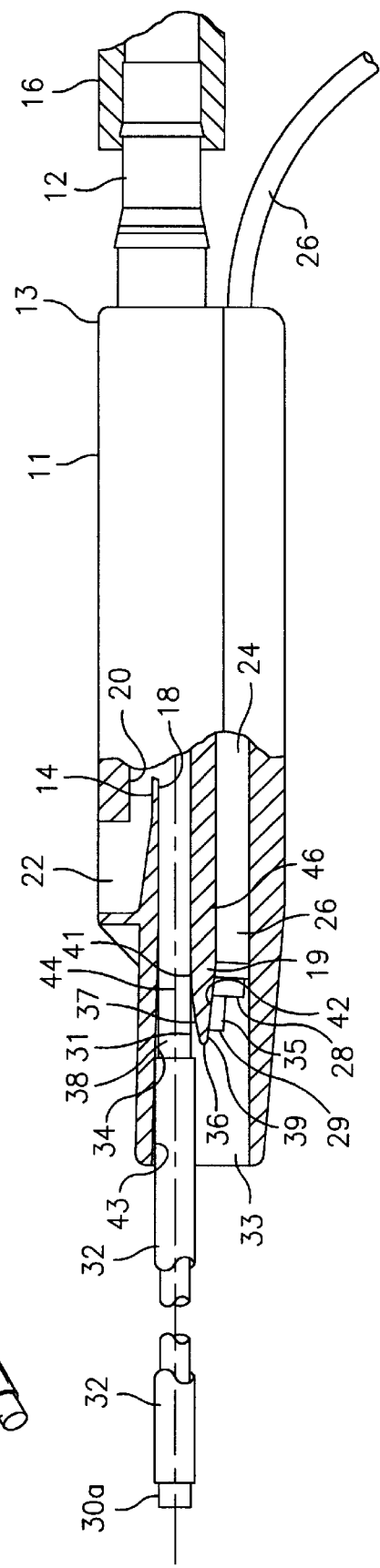

INSTRUMENT FOR SUCTION ELECTROSURGERY

FIELD OF THE INVENTION

This relates to a suction electrosurgery hollow metal tube, and more particularly an insulated hollow metal tube controlled by a body with a suction vent and a method of manufacture. More particularly,

BACKGROUND OF THE DISCLOSURE

U.S. Pat. No. 3,828,780 held by the same assignee as the present disclosure has a combined electrosurgical coagulator suction instrument. That patent is incorporated herein by reference and made a part hereof. The suction electrosurgery hollow metal tube herein is an improvement in the instrument of the '780 patent.

Coagulation of blood vessels during surgery by the application of a high frequency electrical current remains a standard and widely used surgical technique. In this surgery, the tissue of the patient is electrically connected to one side of an electrosurgical circuit while an electrically conductive electrode is connected to the other. When the electrode touches or is near an operative site, a high frequency electrical current flows from the electrode. The energy coagulates at a point where the current arcs from the electrode tip to the patient's tissue.

When this technique seals blood vessels, some quantity of blood will be encountered at the precise region of coagulation. It is therefore often necessary that the excess blood be removed by a suction instrument. Similarly smoke and debris from the electrosurgery should be removed.

The conventional suction instrument takes the form of a plastic body or fitting having a passage connected to a suction source. An elongate hollow metal tube mounted in the body is inserted into the incision to suck out blood or other body fluids. The suction instrument is controlled by a simple vent in the body, the surgeon covering it with a finger when suction is desired in the hollow metal tube and uncovering the vent if suction at the hollow metal tube end is not desired.

The shape of the tip of an electrosurgical coagulator electrode is not critical. Providing an instrument capable of performing electrosurgical coagulation and suction with the hollow metal tube of electrical conductor connected to the electrosurgical coagulating power circuit have been unsatisfactory. This arrangement was unsatisfactory as blood is electrically conductive. If the surgeon places a finger over the vent to induce suction while electrical current flows through the hollow metal tube electrode, blood in the vent conducts current to the finger. The '780 patent addresses that problem as the high frequency currents employed in combination with the thin material of the surgeon's glove offer no effective resistance to the electric current.

Valleylab of Boulder Colo. has sold commercial products exactly like the disclosure of the '780 patent. The exact configuration of the plastic body or fitting thereof provides an insulated handle for the safety and convenience of the surgeon. Several difficulties in the assembly of the hollow metal tube to the plastic body require unnecessary steps and result in a less than ideal fluid tight connection therebetween. The disclosure herein addresses those difficulties with assembly method steps and instrument changes that provide a hereto unknown process for sealingly fitting the hollow metal tube into the body.

SUMMARY OF THE INVENTION

The present invention provides an instrument capable of simultaneous use as an electrosurgical coagulator and as a suction instrument. The instrument may include an elongate body or fitting formed of an inexpensive electrically non-conductive material. A main flow passage could extend longitudinally through the body from end to end with a nipple at one end to couple to a flexible hose connected to a suction source. A second longitudinal passage preferably extends through the body from end to end and receives the electric power cable of the coagulation circuit. The cable most preferably passes entirely through the second passage and its bared end is bent toward the forward end of the main flow passage. A hollow metal tube is in the preferred embodiment inserted into the forward end of the main flow passage. The hollow metal tube can engage the bent bare end folding the end into and against a wall of the flow passage as the hollow metal tube axially seats within the passage. Therefore the hollow metal tube frictionally clamping itself in position for electrically contacting the folded exposed end of the electric power cable.

The preferred embodiment includes a solderless terminal as a spade connector mechanically attached to the bare cable end. Thus the engagement of the hollow metal tube with the spade connector eliminates concerns about fraying, pinching or shearing any one of the multi stranded wires of the bare end. Moreover, the dimensions of the spade connector allows for a repeatable and reliable interference fit with the hollow metal tube and the elongate body wall.

An electrically non conductive insulated sheath encloses the exposed portion of the hollow metal tube except a short portion of the tube tip. Similarly, the portion of the hollow metal tube within the elongate body against the wall and spade connector is exposed. The exposed tip portion is the electrode used to treat the operative site of the patient with electrosurgery. Energy from an electrosurgical generator through the power cable, the solderless terminal, the spade connector and the hollow metal tube flows in the circuit through the tissue and to the other electrode.

The suction source preferably supplies suction to a main flow passage through the interior of the hollow metal tube. A vent regulates the degree of suction in the hollow metal tube. The vent ports do not communicate directly with the main flow passage. A branch passage with a kidney shaped cross section extends from the vent port through the body to communicate with the main flow passage upstream of the vent. During use of the instrument, the vent port and therefore the surgeon's finger are disposed vertically above the main flow passage. The vent is designed or shaped to be completely closed when touched by the surgeon's finger. A relatively long and narrow slot enables the surgeon to regulate the degree of suction by pushing his finger longitudinally along the slot from one end toward the other. Similarly, U.S. Pat. No. 4,686,981, has suction cannula with a large hole and a small hole in the finger plate for at least a two-stage suction control.

The vent offset upstream from the location of its branch passage means, that for blood to reach the vent the blood must flow opposite to the suction. The elongated vent enables the surgeon to apply an adequate amount of suction without complete closing so air flow through the branch passage toward the main passage resists the blood flow from the main passage. The possibility of electric shock or burn at the finger covering the vent is substantially eliminated by preventing blood from reaching the vent.

The improved sealing between the hollow metal tube and the open distal end results from its contour surrounding the hollow metal tube inserted therein and an interior portion thereof formed to assist the folding of the spade connector and the sealing conjugation of the hollow metal tube during axial insert during assembly.

A shelf across an open distal end of the body may intersect a fold line across the spade connector as the hollow metal tube axially engages the spade connector with reverse forces causing backward folding thereof against the shelf. Thus, the spade connector and hollow metal tube lock against one another within the open distal end due to the transverse shelf placement across the distal open end at a place axially set back thereinto. The set back of the shelf facilitates the initiation and complete fold back of the spade connector at the fold line as the hollow metal tube is forced axially into the body. More importantly, the set back results in the locked capture of the spade connector against the shelf.

The shelf includes a cross sectional taper whereby an edge thereof is thinner than a main thickness. The taper provides a folding guide to encourage the formation of the crease at the fold line. The taper may provide camming surfaces for controlling the shape of the fold back. Opposite major surfaces of the shelf extend from the edge to preferably define with the camming surfaces the folded back shape of the spade connector.

Camming surfaces against which the spade connector presses the hollow metal tube during axial assembly wedge it and spade connector within the open distal end forming locked sealing to the interior portion. In particular the open distal end has the transverse tapered shelf in combination with a generally cylindrical surround that receives the hollow metal tube axially during axial assembly. A dimension of the interior portion between the tapered shelf on one side and the generally cylindrical surround on the other tightly engages the axially seated hollow metal tube forcing the hollow metal tube and folded back spade connector together. More importantly, the seal results from general compression due to swaging action between the generally cylindrical surround and the hollow metal tube. In addition, a distal exterior of the body about the open distal end is reduced in cross section preferably having a relatively uniform wall thickness. Thus, the reshaped wall thereabout most preferably has a relatively constant thickness providing a hidden end previously unknown and unappreciated benefit. The assembly of the hollow metal tube and spade connector equalizes radial forces therebetween in all radial directions so compression between the inside of the generally cylindrical surround and the hollow metal tube becomes approximately the same. Likewise the force across the engagement of the hollow metal tube and the spade connector is also equivalent. Concentrations of load are avoided and application of axial force is relatively gentle due to the tapered major camming surfaces. Control of the ultimate retaining force and the seal result directly from the camming surface and radial squeeze provided by the uniform wall thickness of the surround and the placement of the shelf.

The hollow metal tube may be formed of aluminum and has a Brinnel hardness of about 40. The spade connector is preferably stainless steel having a Brinnel hardness of about 200. The tapered shelf is polystyrene plastic such as Dow 478-W. The polystyrene polymer is preferably relatively soft for forming a generally fluid tight seal with the aluminum hollow metal tube. The test results of the seal tightness prove that suction transfer from end to end of the electrosurgical suction hollow metal tube is greater with the disclosed configuration than that of the '780 instrument.

Assembly of electrosurgical suction hollow metal tube into the body of the '780 patent requires that, the wire first be bent with a tool and then the hollow metal tube be inserted to retain the wire. Even with a connector a tool would be used. Bending with the tool and the relatively poor sealing between body interior and hollow metal tube resulted from the location of the shelf axially near the open distal end coupled with the lack of taper on the engaging major shelf surface.

Those difficulties are corrected with the improved design and assembly of the electrosurgical suction tube disclosed herein. The open distal end is shaped to not only sealingly receive and lock the hollow metal tube to the spade connector but also permit the hollow metal tube fold back the spade connector during axial assembly insertion. Installation of the hollow metal tube axially into the generally cylindrical surround transfers adequate force from the hollow metal tube to the spade connector to swing it back upon itself and against the camming surface. The fold back thus takes place as a consequence of the axial assembly of the hollow metal tube into the interior of the body. The stainless steel spade connector folds under the axial force of the softer aluminum hollow metal tube due to the tapered shelf, the direction of the load application and the small cross section of the spade connector.

Other objects and features of the invention will become apparent by reference to the following specification and to the drawings.

BRIEF DESCRIPTION OF THE DRAWINGS

FIG. 2 is a perspective view of the improved electrosurgical suction tube of the present disclosure.

FIG. 4 is a side view in cross section of the electrosurgical suction tube of FIG. 2 as would be seen if cut along line 4—4 of FIG. 2.

DETAILED DESCRIPTION OF THE INVENTION

Components are numbered with the same number and are named identically but in the description of the improvements different numbers and revised terminology appear.

Figure 1:
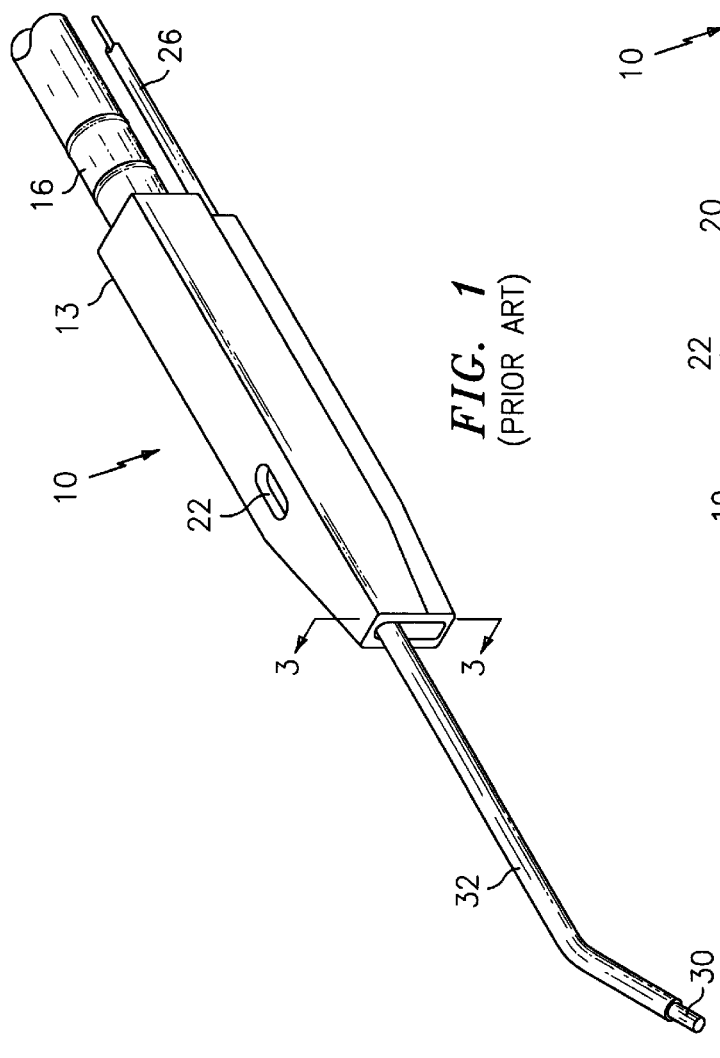
FIG. 1 is a perspective view of the prior electrosurgical suction tube of U.S. Pat. No. 3,828,780.
Figure 3:
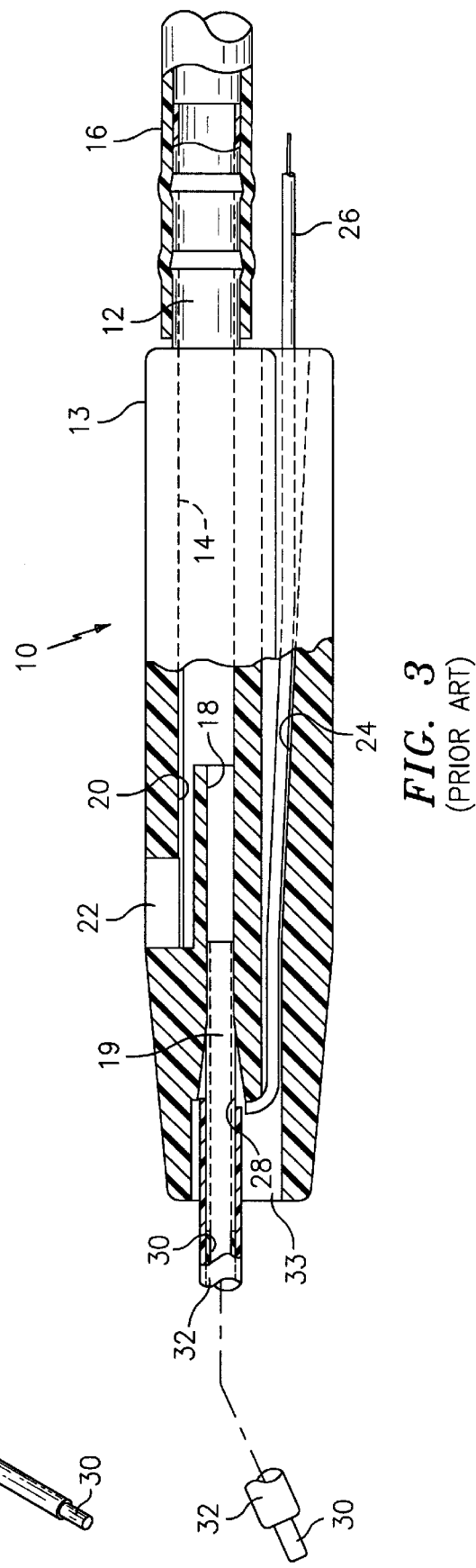
FIG. 3 is a side view in cross section of the electrosurgical suction tube of FIG. 1 as would be seen if cut along line 3—3 in FIG. 1.

The instrument of the present invention includes an elongate body 10 in FIGS. 1 and 3. The improved elongate body 11 appears in FIGS. 2 and 4. The elongate body 10 or 11 is preferably molded or otherwise formed from a relatively inexpensive electrically non-conductive material such as Dow 478W Polystyrene plastic. FIGS. 1 and 3 disclose the prior instrument and FIGS. 2 and 4 depict the present invention. As is usually the case with instruments of this type, the instrument is designed to be disposed of after a single usage. By molding the body from relatively inexpensive thermoplastic material production costs are well within a "throw-away" category. Consequently and favorably the improvement reduces the material needed to form the elongated body 10 or 11 and the steps required to assemble the instrument.

A projecting nipple 12 is integrally formed at the rearward end 13 of body 10 or 11 so a main flow passage 14 extends through the nipple 12 for the entire length of the body 10 or 11. Nipple 12 connects passage 14 to a flexible tube 16 whose opposite end attaches to a conventional suction source, not shown. As best seen in FIGS. 3 and 4, the forward or left hand end 18 of main passage 14 is of reduced diameter. Left hand end 18 separates from a branch passage 20 so main passage 14 communicates with an elongate vent 22 that opens at the exterior of body 10 or 11. The branch passage 20, located vertically above the main flow passage 14 so during use material within the body 10 or 11 flows into the left hand end 18 but not readily into branch passage 20, see FIGS. 3 and 4.

A second passage 24 extends through body 10 or 11 from end to end with dimensions to receive an electric power cable 26. Power cable 26 connects to the electrical power supply used in, for example, coagulation of tissue and bodily fluids. Insulation stripped from the end of cable 26 bares end 28 and that is bent back to extend rearwardly into the forward end of main passage section 18 as shown in FIG. 3. In FIG. 4 the stripped cable 26 at bare end 28 has a solderless terminal in the form of a spade connector 29 crimped thereto as shown in FIG. 4. A hollow metal tube 30 is axially inserted into an open distal end 33 of main passage section 18 in FIGS. 3 and 4.

The hollow metal tube 30 is dimensioned to snugly fit into passage 18. Exterior wall 31 of the hollow metal tube 30 clamps the spade connector 29 and wall 19 of passage section 18 when hollow metal tube 30 is seated in body 11 establishing electrical contact between hollow metal tube 30 and the electric power source.

Vent 22 is a narrow elongate slot longitudinally of the elongate body 10 or 11 as in FIGS. 3 and 4. When suction is supplied to tube 16, with vent 22 open, the suction is substantially all vented through opening 22 so little suction is supplied to the interior of hollow metal tube 30. When it is desired to suck blood or other body fluids into hollow metal tube 30, the surgeon's finger slid forward over vent 22 provides the desired degree of suction. In FIGS. 3 and 4, fluid flowing through the instrument passes from left to right through passage 18 in an upstream direction from the location at which branch passage 20 opens into main passage 14. For any blood to flow through branch passage 20 toward vent 2 the blood must flow in a direction opposite to the direction of flow induced by the suction applied at tube 16. Suction can be applied at the same time current flows through hollow metal tube 30 without risking electrical shock or burn to the portion of the finger exposed over vent 22.

In FIGS. 1 to 4, the middle portion of hollow metal tube 30 is enclosed by a sheath of electrically non-conductive material 32. A relatively short section at the extreme tip 30a of the hollow metal tube 30 and part at the opposite end are exposed. In FIG. 3 the bared end 28 makes electrical contact. Wall 19 has a slight upwardly facing taper designed to provide room for the bent cable 26 bared end 28, as shown in FIG. 3.

In FIG. 4, the hollow metal is similarly shown with the improved spade connector 29. The improved sealing to the hollow metal tube 30 within open distal end 33 of the elongate body 11 results from an interior portion 34 shaped to surround the hollow metal tube 30 inserted therein. Interior portion 34 is formed to assist the folding of the spade connector 29 and the sealing conjugation of the hollow metal tube 30 during axial insert during assembly.

In FIG. 4 shelf 35 across the open distal end 33 of the elongate body 11 intersects at a fold line 36 on the spade connector 29. The hollow metal tube 30 axially engages the spade connector 29 with reverse forces causing backward folding and sliding compression of the spade connector 29. A crease 37 forms against the shelf 35 due to the hollow metal tube 30 insertion. The spade connector 29 and hollow metal tube 30 lock against one another and within the open distal end 33. Transverse placement of the shelf 35 is across the distal open end 33 at a place 38 axially set back into the open distal end 33. The set back of the place 38 facilitates the initiation and complete fold back of the spade connector 29. The fold at the fold line 36 forms crease 37 as the hollow metal tube 30 is forced axially into the elongate body 11. More importantly, the set back place 38 results in the locked capture of the spade connector 29 against the shelf 35 as shown in FIG. 4.

The shelf 35 includes a cross sectional taper whereby an edge 39 thereof is thinner than a main thickness 40. The edge 39 of the taper provides a folding guide to encourage the formation of the crease 37 at the fold line 36. The taper may provide camming surfaces 41 and 42 for controlling the shape of the fold back. Camming surfaces 41 and 42 are opposite one another and are the major surfaces of the shelf 35. Camming surfaces 41 and 42 extend from edge 39 to define the folded back and shape of the spade connector 29.

Camming surfaces 41 and 42 wedge the spade connector 29 folded by the hollow metal tube 30 during axial assembly in the open distal end 33 to form locked sealing to the interior portion 34. In particular the open distal end 33 has the transverse tapered shelf 35 in combination with a generally cylindrical surround 43 that receives the hollow metal tube 30 axially during axial assembly seen in FIGS. 2 and 4. Internal dimension 44 between the tapered shelf 35 and the generally cylindrical surround 43 tightly receives the axially inserted hollow metal tube 30 and folded spade connector 29 and retains the assembly thereof. More importantly, sealing results from general compression due to swaging action between the generally cylindrical surround 43 and the hollow metal tube 30. In addition, a distal exterior 45 of the elongate body 11 about the open distal end 33 is reduced in cross section preferably having a relatively uniform wall thickness as shown in FIG. 2. Thus, the reshaped wall thereabout has a relatively constant thickness providing an unknown advantage previously unappreciated. Assembly of the hollow metal tube 30 and spade connector 29 in open end 33 radially forces the components equally in radial directions. The inside of the generally cylindrical surround 43 and the hollow metal tube 30 compress approximately the same amount. Likewise the force across the engagement of the hollow metal tube 30 and the spade connector 29 is also equivalent. Stress concentrations are avoided. Thus application of axial force during insertion remains relatively gentle due to the tapered camming of opposed surfaces 41 and 42. The ultimate retaining force and the seal result from the taper and radial squeeze between the general cylindrical surround 43 and the hollow metal tube 30.

The hollow metal tube 30 in the preferred embodiment is formed of aluminum having a Brinnel hardness of about 40. The spade connector 29 is preferably stainless steel having a Brinnel hardness of about 200. The tapered shelf 35 is softer as it is molded of polystyrene plastic such as Dow 478-W. The polystyrene polymer is relatively soft for forming a generally fluid tight seal with the aluminum hollow metal tube 30. The test results of the seal tightness prove that suction transfer through the hollow metal tube 30 is greater with the disclosed improved configuration than in the instrument disclosed in the '780 patent.

The testing procedure followed to prove that, improved performance of the instrument of FIGS. 2 and 4 over that of FIGS. 1 and 3 used a time measurement of that needed to draw a measured amount of fluid. With the vacuum source set at 12 inches of mercury each pencil was connected to the vacuum source one at a time. The pencil electrode was applied to a water supply container and then the timer was started. When the pencil has evacuated 1000 ml of water into a suction canister the timer was stopped and the results were recorded. This procedure was repeated using each pencil. With testing complete it was found that the '780 instrument took about nine percent longer to draw the fluid.

Before hollow metal tube 30 insertion into the elongate body 10, in FIGS. 1 and 3, bare end 28 must be bent with a tool so the hollow metal tube 30 can then be inserted to retain bare end 28. The bending with the tool is an added step and caused relatively poor sealing between body interior and hollow metal tube 30. The location of the wall 19 in FIG. 3, axially near the open distal end 33 and lack of taper on the bottom thereof resulted the need to bend with a tool. Even with a tool bent spade connector 29, elongate body 10 of FIG. 3, lack axially placement of wall 19 and bottom taper so two steps of bending were required to make the fold.

Those manufacturing difficulties are corrected with the improved design and assembly of the electrosurgical suction tube disclosed herein. The open distal end 33 is shaped to sealingly receive and lock the hollow metal tube 30 to the spade connector 29. The hollow metal tube 30 folds back the spade connector 29 at the crease 37 during axial assembly insertion without the need of a tool to bend. Axial installation of hollow metal tube 30 into generally cylindrical surround 43 transfers adequate force there from to spade connector 29 swinging it back upon itself and against the camming surfaces 41 and 42. The fold back takes place as a result of the step of axial assembly of hollow metal tube 30 into the interior of the elongate body 11 as shown assembled and in cross section in FIG. 4. Surprisingly stainless steel spade connector 29 folds under the axial force of the softer aluminum hollow metal tube 30. Because of the tapered shelf 35, the direction of the load application thereagainst and the relatively small cross sectional area of the spade connector 29 about its fold line 36 folding occurs.

An instrument constructed with the following dimensions has been found to be particularly suitable for use in accordance with the disclosure herein.

While one embodiment of the invention has been described in detail, it will be apparent to those skilled in the art that the disclosed embodiment may be modified. Therefore, the foregoing description is to be considered exemplary rather than limiting, and the true scope of the invention is that defined in the following claims.

What is claimed is:

1. An instrument for attachment to suction and an electrosurgical power supply, the instrument for use by a surgeon on a patient comprising:
   an elongate body molded of plastic material and with a rearward end;
   a projecting nipple at the rearward end;
   a main flow passage extending through the nipple and for the entire length of the elongate body;
   a flexible tube attached to the nipple for attachment to and the suction;
   a hollow metal tube extending from the elongate body and adapted to be attached to the electrosurgical power supply and in fluid communication with the main flow passage, the hollow metal tube substantially insulated;
   a vent accessible to the surgeon and connected through the elongate body to communicate with the main flow passage and the hollow metal tube;
   a tip on the hollow metal tube extending from the elongate body, the tip uninsulated for passing electrosurgical energy to the patient;
   an open distal end on the elongate body opposite the rearward end for receiving the hollow metal tube therewithin;
   a shelf across the main flow passage for engaging and holding the hollow metal tube therewithin, the shelf having opposed tapered camming surfaces, the shelf set back from the open distal end of the elongate body;
   an edge on the shelf within the open distal end and between the opposed camming surfaces;
   an insulated cable adapted to be coupled to the power supply and passing through the elongate body to the shelf, and
   a generally cylindrical surround about the open distal end of the elongate body, the generally cylindrical surround attached to the shelf;
   an interior portion defined by the generally cylindrical surround and the shelf for receiving the hollow metal tube, and
   a spade connector at the shelf end of the insulated cable, the spade connector bent at a fold line thereacross to wrap around the edge of the shelf for wedged capture in a locking seal conforming within a interior portion between the camming surface and the hollow metal tube when the spade connector wraps about the edge.

2. The instrument of claim 1 wherein the spade connector is stainless steel and the hollow metal tube is aluminum.

3. The instrument of claim 2 wherein the hardness of the aluminum is of about Brinnel hardness 40.

4. The instrument of claim 2 wherein the hardness of the stainless steel is of about Brinnel hardness 200.

5. The instrument of claim 1 wherein the elongate body is a polymer and the generally cylindrical surround is of relatively uniform wall thickness.

6. The instrument of claim 5 wherein the generally cylindrical surround and the shelf define the interior portion and the open distal end for receiving and holding the hollow metal tube and the elongate body together so the main flow passage is in substantially fluid communication with the hollow metal tube for transmission of suction between the nipple and the tip.

7. The instrument of claim 6 wherein the shelf within and across the open distal end has the edge axially spaced proximally of the open distal end, the edge for engagement with the spade connector during insertion of the hollow metal tube to fold back the spade connector as the hollow metal tube is received within the interior portion and the shelf camming surface for capturing the folded spade connector against the hollow metal tube inserted within the generally cylindrically surround and against the camming surface of the shelf.

8. The instrument of claim 7 wherein the generally cylindrical surround is of relatively uniform wall thickness so radial forces on the inserted hollow metal tube are equal in radial directions and compression between the inside of the generally cylindrical surround and the hollow metal tube becomes approximately the same in all radiating directions when the camming surface engages the spade connector and the hollow metal tube.

9. The instrument of claim 1 wherein the hollow metal tube and the main flow passage are generally aligned with one another but not coaxial and the vent interconnects them for fluid communication therethrough.

10. The instrument of claim 1 wherein the vent is shaped to allow the surgeon to controllably bypass suction permitting suction control at the tip of the hollow metal tube during electrosurgery allowing the surgeon to regulate the rate of removal of smoke, blood and debris resulting from electrosurgery on the patient.

11. An instrument for attachment to suction and an electrosurgical power supply, the instrument for use by a surgeon on a patient comprising:

an elongate molded polymer body with a rearward end;

a projecting nipple at the rearward end;

a main flow passage extending through the nipple and for the entire length of the elongate body;

a flexible tube attached to the nipple for attachment to the suction;

a hollow metal aluminum tube extending from the elongate body and adapted to be attached to the electrosurgical power supply and in fluid communication with the main flow passage, the hollow metal tube substantially insulated;

a tip on the hollow metal tube extending from the elongate body, the tip uninsulated for passing electrosurgical energy to the patient;

an open distal end on the elongate body opposite the rearward end for receiving the hollow metal tube therewithin;

a vent accessible to the surgeon and connected through the elongate body to communicate with the main flow passage and the hollow metal tube, the hollow metal tube and the main flow passage are generally aligned with one another but not coaxial, the vent shaped to allow the surgeon to controllably bypass suction permitting suction control through the hollow metal tube during electrosurgery, the vent shape allowing the surgeon to regulate the rate of removal of smoke, blood and debris resulting from electrosurgery on the patient;

a shelf across the open distal end for engaging and holding the hollow metal tube within the open distal end, the shelf having opposed tapered camming surfaces, the shelf set back from the open distal end of the elongate body;

a generally cylindrical surround about the open distal end of the elongate body, the generally cylindrical surround attached to the shelf, the generally cylindrical surround of relatively uniform wall thickness so radial forces on the inserted hollow metal tube are equal in radial directions and compression between the inside of the generally cylindrical surround and the hollow metal tube becomes approximately the same in all radiating directions;

an interior portion defined by the generally cylindrical surround and the shelf for receiving the hollow metal tube, so the main flow passage is in substantially fluid communication with the hollow metal tube for transmission of suction between the nipple and the tip;

an insulated cable adapted to be coupled to the power supply and passing through the elongate body to the shelf;

a spade connector at the shelf end of the insulated cable;

an edge on the shelf within the interior portion and between the opposed camnning surfaces, the edge axially spaced proximally of the open distal end, the edge for engagement with the spade connector during insertion of the hollow metal tube to fold back the spade connector as the hollow metal tube is received within a interior portion and the shelf camming surface for capturing the folded spade connector against the hollow metal tube inserted within the generally cylindrically surround and against the camming surface of the shelf, the spade connector bent at a fold line thereacross to wrap around the edge of the shelf for wedged capture in a locking seal conforming capture within the interior portion between the camming surface and the hollow metal tube when the spade connector wraps about the edge when the camming surface engages the spade connector and the hollow metal tube to electrically contact the spade connector and the hollow metal tube.

* * * * *